United States Patent [19]
Couval et al.

[11] Patent Number: 5,776,986
[45] Date of Patent: Jul. 7, 1998

[54] COMPOSITION CONTAINING RETINAL

[75] Inventors: Emmanuelle Couval, Ramonville Saint Agne; Nicole Peyrot, Toulouse; Nathalie Firmino, Ramonville Saint Agne; Henri Jammes; Valérie Clairand, both of Toulouse, all of France

[73] Assignee: Pierre Fabre Dermo-Cosmetique, Boulogne, France

[21] Appl. No.: 716,221

[22] PCT Filed: Mar. 22, 1995

[86] PCT No.: PCT/FR95/00350

§ 371 Date: Sep. 20, 1996

§ 102(e) Date: Sep. 20, 1996

[87] PCT Pub. No.: WO95/25507

PCT Pub. Date: Sep. 28, 1995

[30] Foreign Application Priority Data

Mar. 22, 1994 [FR] France .................. 94 03339

[51] Int. Cl.$^6$ ............................................. A61K 31/07
[52] U.S. Cl. .................................. 514/698; 514/970
[58] Field of Search ............................. 514/698, 970

[56] References Cited

U.S. PATENT DOCUMENTS 5,093,360   3/1992   Yu et al. ................... 514/463

FOREIGN PATENT DOCUMENTS

| 2 247 203 | 4/1974 | European Pat. Off. |
| 094 771 | 5/1982 | European Pat. Off. |
| 330 496 | 2/1989 | European Pat. Off. |
| 408 370 | 7/1990 | European Pat. Off. |
| 93/00085 | 6/1991 | WIPO |

*Primary Examiner*—Rebecca Cook
*Attorney, Agent, or Firm*—The Firm of Gordon W. Hueschen

[57] ABSTRACT

A retinal-containing cosmetic skin-care composition comprising an oil-in-water emulsion stabilized by BHT and a method for preparing same.

6 Claims, No Drawings

COMPOSITION CONTAINING RETINAL

This is a 371 of PCT/FK95100250 filed Mar. 22, 1995.

The present invention relates to new dosage forms suitable for topical application and containing retinal.

Health-care products containing retinoids have become a focus of interest in recent years. Retinoic acid, also known by the name of vitamin A acid or tretinoin, is used in the treatment of acne, and compositions containing vitamin A acid are numerous and varied.

More recently, other applications of retinoids have been put forward, for instance light-induced aging. In effect, individuals who are exposed to large amounts of sunlight during their childhood display the following skin features in adulthood: wrinkled, furrowed, yellow, slack, rough, dry and blemished (hyperpigmentation) skin and various premalignant growths. These phenomena are more marked in fair-skinned individuals, who often burn in the sun and do not tan very much.

Before these skin manifestations appear clinically, serious adverse changes in the epidermis and dermis may be observed microscopically in young subjects who have received a large amount of exposure.

U.S. Pat. No. 4,603,146 describes the treatment of skin damaged by exposure to sunlight, using a preparation containing vitamin A acid in an emollient excipient. Later, in U.S. Pat. No. 4,877,805, it is taught that retinoids may be used to prevent and repair the damage caused by sunlight on human skin.

It is also known that the use of retinal (vitamin A aldehyde) is preferred to that of retinoic acid on account of its better skin tolerability. In effect, retinal (vitamin A aldehyde) occurs naturally in human metabolism: it is used, in particular, in treatments designed to improve vision.

However, retinal is a compound displaying poor physicochemical stability; its formulation in a form displaying good organoleptic qualities as well as good storage characteristics has not been achieved satisfactorily to date.

In the context of the present invention, the active retinal may be in 13-cis or 13-trans form or the form of all other mixtures of these isomers.

On storage, other forms tend to appear, such as 9-cis-retinal, 11-cis-retinal or condensation products of the polymer type, which are inactive.

U.S. Pat. No. 4,826,828 has proposed the use of volatile silicones and ethanol for the preparation of compositions containing retinol; these preparations may be diluted before application by formation of a water-in-oil emulsion.

U.S. Pat. No. 4,720,353 describes water-in-oil emulsions stabilized by a particular organopolysiloxane.

However, these formulations do not give satisfactory results on storage.

Application WO 93/00085 describes formulations of retinoids in the form of a water-in-oil emulsion, stabilized by a complex system comprising a chelating agent and water-soluble and fat-soluble antioxidant.

These formulations entail a large number of parameters which are difficult to implement. In addition, water-in-oil emulsions are poorly suited to topical application, especially in cosmetology.

Accordingly, the subject of the present invention is a dermocosmetological composition containing retinal, characterized in that it consists of an oil-in-water emulsion stabilized essentially by one or more fat-soluble antioxidants.

Oil-in-water emulsions according to the present invention possess good spreading capacities without a greasy feel. The specific stabilization system enables the phenomena of degradation over time which are observed with the conventional oil-in-water emulsions to be limited.

Antioxidants which are especially suitable for obtaining a stabilization system according to the invention may be chosen from the group comprising: butylated hydroxytoluene (BHT), butylated hydroxyanisole (BHA), ascorbyl palmitate, alpha-tocopherol and its esters, citric acid, propyl gallate and/or mixtures thereof.

The alpha-tocopherol may be, in particular, in acetate form.

The retinal present in the composition is incorporated in the oily (internal) phase of the emulsion. The retinal will thus be better protected from aerial oxygen than if it were in the external phase (in a water-in-oil emulsion, for example) and hence in direct contact with the air.

In general, the retinal concentration in the composition according to the invention is at least 0.01% by weight, and can reach as much as approximately 1% by weight of the total composition.

Preferred concentrations for the retinal are between 0.04 and 0.06% by weight, and will be more especially approximately 0.05%.

Preferably, the concentration of fat-soluble antioxidants in the oily phase is between 0.005% and 0.5% by weight.

These concentrations will vary in accordance with the antioxidant used. For example, BHT or BHA will each be present at approximately 0.01% to 0.03% by weight. The concentrations of alpha-tocopherol or its esters can reach 0.5%, and are preferably greater than 0.05%, by weight.

An important factor for the stability of the emulsions is the ratio of the concentrations of fat-soluble antioxidants to the retinal concentrations. Especially advantageous results in terms of stability on storage are obtained when the fat-soluble antioxidant/-retinal concentration ratio is between 0.1 and 0.6, in particular when the ratio is approximately 0.4.

The oily phase can contain mineral and/or organic oils, polar or otherwise, waxes, esters and silicones. Depending on the desired physical characteristics, the compositions according to the invention can also contain surfactants, gelling thickeners, perfumes and colorants.

The pH of the compositions is preferably slightly acid or close to neutrality for the purpose of its |sic| application to the skin; compositions according to the invention have, in particular, a pH of between 6 and 7.5.

According to one of its aspects, the subject of the invention is an oil-in-water emulsion, characterized in that it contains retinal at a concentration of between 0.04% and 0.06% by weight, preferably of approximately 0.05%, and BHT at a concentration of between 0.01% and 0.03%, preferably of approximately 0.02%, by weight.

According to yet another aspect, the invention relates to an oil-in-water composition, characterized in that it contains retinal at a concentration of between 0.04% and 0.06% by weight, preferably of approximately 0.05%, and propyl gallate at a concentration of between 0.01% and 0.03%, preferably of approximately 0.02%, by weight.

The invention comprises the cosmetic use of the oil-in-water emulsions thus defined.

It also comprises the use as medicament of the retinal-based compositions displaying one or more of the above features.

Lastly, the present invention also extends to a process for preparing the oil-in-water compositions, which entails the following steps:

a) retinal is dissolved in one or more organic and/or mineral oils, b) one or more fat-soluble antioxidants is/are added to the solution, c) the solution obtained is emulsified in an aqueous and/or aqueous-alcoholic solution to obtain an oil-in-water emulsion.

The examples which follow are designed to illustrate the invention without in any way limiting its scope.

EXAMPLE 1

Qualitative study of stabilization of retinal

In a first stage, different lipophilic antioxidants were tested in order to define the one which stabilizes retinal best:

The antioxidants tested are:

| | |
|---|---|
| ● BHA | Butylated hydroxyanisole |
| ● BHT | Butylated hydroxytoluene |
| ● PROPYL GALLATE | |
| ● RONOXAN(R) A | Alpha-tocopherol 5% |
| | Ascorbyl palmitate 25% |
| | Q. S. lecithin |
| ●0 RONOXAN(R) 582 | Ascorbyl palmitate 15% |
| | Mono- and diglyceride 85% |
| ● RONOXAN(R) 583 | Ascorbyl palmitate 11% |
| | Alpha-tocopherol 11% |
| | Citric acid 3% |
| | Mono- and diglyceride 75% |
| ● ALPHA-TOCOPHEROL | |
| ● ACETATE | |
| ● TOCOPHEROL | |

Retinal (vitamin A aldehyde) is solubilized at a concentration of 0.05% in 2 oils: one polar, namely Miglyol® 812 (caprylic triglycerides), the other nonpolar, namely Cosbiol® (squalane).

Results

TABLE 1

0.05% solution of retinal (vitamin A aldehyde) in a polar oil (Miglyol(R) 812: capric/caprylic triglycerides).

| Antioxidant | Storage at room temp. ≅ 20° C. | Amount of trans-retinal remaining (%) |
|---|---|---|
| BHA, 0.01% | T 1 month | 92.8% |
| | T 6 months | 76% |
| BHT, 0.01% | T 1 month | 92.4% |
| | T 6 months | 78.4% |
| PROPYL GALLATE 0.01% | T 1 month | 91.4% |
| | T 6 months | 73.7% |
| RONOXAN(R) A 0.1% | T 1 month | 90% |
| | T 6 months | 60.2% |
| RONOXAN(R) 582 0.1% | T 1 month | 94.1% |
| | T 6 months | 78.4% |
| RONOXAN(R) 583 0.1% | T 1 month | 88.2% |
| | T 6 months | 75.2% |
| ALPHA-TOCOPHEROL ACETATE + TOCOPHEROL 0.2% | T 1 month | 90.7% |
| | T 6 months | 73.8% |
| Control without antioxidant | T 1 month | 81.3% |
| | T 6 months | 41.4% |

TABLE 2

0.05% solution of retinal (vitamin A aldehyde) in a nonpolar oil (Cosbiol: squalane).

| Antioxidant | Storage at room temp. ≅ 20° C. | Amount of trans-retinal remaining (%) |
|---|---|---|
| BHA, 0.01% | T 1 month | 99.4% |
| | T 6 months | 75% |
| BHT, 0.01% | T 1 month | 94.8% |
| | T 6 months | 73.5% |
| PROPYL GALLATE 0.01% | T 1 month | 97.3% |
| | T 6 months | 76.4% |
| RONOXAN(R) A 0.1% | T 1 month | 90.55% |
| | T 6 months | 69.6% |
| RONOXAN(R) 582 0.1% | T 1 month | 91.44% |
| | T 6 months | 69.7% |

TABLE 2-continued 0.05% solution of retinal (vitamin A aldehyde) in a nonpolar oil (Cosbiol: squalane).

| Antioxidant | Storage at room temp. ≅ 20° C. | Amount of trans-retinal remaining (%) |
|---|---|---|
| RONOXAN(R) 583 | T 1 month | 98.2% |
| | T 6 months | 78.5% |
| ALPHA-TOCOPHEROL ACETATE + TOCOPHEROL 0.2% | T 1 month | 91.9% |
| | T 6 months | 76.2% |
| Control without antioxidant | T 1 month | 85.6% |
| | T 6 months | 43.7% |

Conclusion

The qualitative study of the lipophilic antioxidants in relation to the stabilization of retinal (vitamin A aldehyde) reveals good results with RONOXAN 582, RONOXAN 583, PROPYL GALLATE, BHA and BHT, in both of the solvents Miglyol 812® (R) and Cosbiol.

EXAMPLE 2

Qualitative study of protection of a mixture of fats

A systematic study of protection against oxidation of a mixture of fats and its emulsifying system was carried out with the same antioxidants as those described in the preceding section.

The fatty phase adopted corresponds to an optimal cosmetic mixture, which will be introduced subsequently into an aqueous phase to produce an oil-in-water emulsion.

The composition of this phase is as follows:

| | |
|---|---|
| ● Neobee 18(R) hybrid safflower oil | 10 g |
| ● Heavy liquid petrolatum | 5 g |
| ● Cremophor RH 40(R) | |
| ● (hydrogenated and ethoxylated castor oil) | 1 g |
| ● Simulsol 165(R) | |
| ● (PEO glycerol monostearate) | 8.5 g |
| ● Wax E (microcrystalline) | 1.5 g |
| ● Acetulan(R) (acetylated lanolin alcohols) | 2 g |
| ● Neobee M5(R) (coconut triglycerides) | 9 g |
| ● Solulan PB 10(R) | |
| ● (propoxylated lanolin ether) | 1.5 g |
| ● 2-Phenoxyethanol | 0.5 g |
| ● Methyl para-hydroxybenzoate | 0.2 g |
| ● Butyl para-hydroxybenzoate | 0.1 g |
| Total | 39.3 g |

NB The aqueous phase which will be added subsequently will constitute 60.7% of the formula, making 100% in total Results The peroxide value was assayed at time 0 and after months of storage at room temperature in the region of 20 C.

| Mixture of fats and the emulsifying system in g | | Antioxidant | Peroxide value | |
|---|---|---|---|---|
| | | | T0 | T6 month |
| Neobee 18 | 10 | BHA 0.01 g | 7.93 | 10.13 |
| Heavy liquid petrolatum | 5 | BHT 0.01 g | 7.78 | 7.65 |
| Cremophor RH 40 | 1 | PROPYL GALLATE 0.01.g | 7.73 | 8.84 |

| Mixture of fats and the emulsifying system in g | | Antioxidant | Peroxide value | |
|---|---|---|---|---|
| | | | T0 | T6 months |
| Simulsol 165 | 8.5 | | | |
| Wax E | 1.5 | RONOXAN A(R) | 8 | 6.33 |
| Acetulan | 2 | 0.1 g | | |
| Neobee M5 | 9 | RONOXAN 582(R) | 7.48 | 6.59 |
| Solulan PB 10 | 1.5 | 0.1 g | | |
| 2-Phenoxyethanol | 0.5 | RONOXAN 583(R) | 6.67 | 9.83 |
| Methyl para-hydroxybenzoate | 0.2 | 0.1 g | | |
| Butyl para-hydroxybenzoate | 0.1 | ALPHA-TOCOPHEROL ACETATE 0.1 g | 8.57 | 9.48 |
| | | ALPHA TOCOPHEROL 0.1 g | 7.26 | 20.66 |
| | | Control without antioxidant | 9 | 30.52 |

Conclusion

This study of protection against oxidation of a mixture of fats reveals good results with RONOXAN® 582, RONOXAN® 583, propyl gallate, BHA and alphatocopherol acetate, and BHT in particular.

EXAMPLE 3

Quantitative study with BHT

A quantitative study of stabilization of retinal in an oil-in-water emulsion was conducted with BHT (butylated hydroxytoluene), which had given very good results in the preceding study.

The emulsion adopted was stored for 6 months at room temperature (in the region of 20° C.).

The retinal was assayed in the emulsion at different storage times.

Form of the oil-in-water emulsion

| (Formula 1 | Retinal | 0.05% |
|---|---|---|
| (Formula 2 | Retinal | 0.025% |

Fatty phase

| BHT | 0.01% |
|---|---|
| Neobee 18 | 10% |
| Heavy liqiiid petrolatum | 5% |
| Cremophor RH 40 | 1% |
| Simulsol 165 | 8.50% |
| Wax E | 1.50% |
| Acetulan | 2% |
| Neobee M5 | 10% |
| Solulan PB 10 | 1.50% |
| 2-Phenoxyethanol | 0.50% |
| Methyl para-hydroxybenzoate | 0.20% |
| Triethanolamine | 0.30% |

Aqueous phase

| Propylene glycol | 3% |
|---|---|
| Carbopol 934 | 0.25% |
| Purified water qs | 100% |
| pH: in the region of 7 | |

| | % of trans-retinal remaining | |
|---|---|---|
| | Formula 1 | Formula 2 |
| T 1 month | 98.9% | 98.8% |
| T 2 months | 98% | 96.9% |
| T 3 months | 96% | 94.9% |
| T 6 months | 83% | 92.9% |

Conclusion

The excellent results recorded at 6 months, in particular with the formula 2, reveal a good protection of the retinal with BHT in the ratio 0.01/0.025

BHT/retinoid

The order of magnitude of this ratio is preserved in the finished product.

Retinal was determined by high performance liquid chromatography under the following conditions:

Apparatus equipped with a normal silica column (5 μ), length 25 cm, internal diameter 0.4 cm, with a variable wavelength detector set at 365 nm.

The eluent phase is composed of 99% hexane, dioxane and isopropanol in the proportions 990:10:1. Its flow rate is 1.5 ml/min.

The sample to be analyzed is dissolved in dioxane, then in isopropanol and in hexane in the proportions of the eluent phase and at a concentration of 1 μg/ml. 20 μl of solution to be analyzed are injected into the chromatograph in isocratic mode and at room temperature: the retinal emerges with a retention time in the region of approximately 7.5 min.

The HPLC results are reproducible with a coefficient of variation of 2.4%.

EXAMPLE 4

Study of the stabilization of retinal in an oil-in-water emulsion

Detailed formula
Aqueous phase

| Purified water gs | 100% |
|---|---|
| Carbopol 934 | 0.25% |
| Propylene glycol | 3% |

Fatty phase

| Neobee 18 | 10% |
|---|---|
| Heavy liquid petrolatum | 5% |
| Cremophor RH 40 | 1% |
| Simulsol 165 | 8.50% |
| Wax E flakes | 1.50% |
| Acetulan | 2% |
| Neobee M5 | 10% |
| Solulan PB 10 | 1.50% |
| BHT | 0.02% |
| 2-Phenoxyethanol | 0.50% |
| Methyl para-hydroxybenzoate | 0.20% |
| Triethanolamine | 0.30% |
| pH: in the region of 7 | |

Results

The emulsion was stored for 18 months at room temperature (in the region of 20° C.), and for 6 months at 40° C. in accelerated aging.

| Storage | % of trans-retinal remaining |
| --- | --- |
| 4 months at room temp. | 100% |
| 4 months at 40° C. | 86% |
| 6 months at room temp. | 95.5% |
| 6 months at 40° C. | 79% |
| 12 months at room temp. | 80% |
| 18 months at room temp. | 76% |

Conclusion

The proposed emulsion displays excellent stability of the retinal, with 95.5% of trans-retinal after 6 months at 40° C. and 76% after 18 months at room temperature.

EXAMPLE 5

Formulation examples

Formula A

| | |
| --- | --- |
| 1. Retinal (trans form) | 0.05% |
| 2. Hybrid safflower oil (Neobee 18) | 10% |
| 3. Heavy liquid petrolatum | 5% |
| 4. Coconut triglycerides (Neobee M5) | 10% |
| 5. Ethoxylated hydrogenated castor oil (Cremophor RH 40) | 1% |
| 6. Glycerol monostearate/PEO (Simulsol 165) | 8.5% |
| 7. Microcrystalline wax (Wax E) | 1.5% |
| 8. Acetylated lanoline alcohols (Acetulan) | 2% |
| 9. Propoxylated lanoline ether (Solulan PB 10) | 1.5% |
| 10. Butylated hydroxytoluene | 0.02% |
| 11. 2-Phenoxyethanol | 0.5% |
| 12. Propyl para-hydroxybenzoate | 0.4% |
| 13. Butyl para-hydroxybenzoate | 0.2% |
| 14. Carbopol 934 | 0.25% |
| 15. Propylene glycol | 3% |
| 16. Triethanolamine qs   pH ≅ 6.5 | 0.3% |
| 17. Purified water qs | 100 |
| | pH: in the region of 6.5 |

Formula B

| | |
| --- | --- |
| 1. Retinal (trans form) | 0.05% |
| 2. Hybrid saf flower oil (Neobee 18) | 10% |
| 3. Heavy liquid petrolatum | 5% |
| 4. Coconut triglycerides (Neobee M5) | 10% |
| 5. Ethoxylated hydrogenated castor oil (Cremophor RH 40) | 1% |
| 6. Glycerol monostearate/PEO (Simulsol 165) | 8.5% |
| 7. Microcrystalline wax (Wax E) | 1.5% |
| 8. Acetylated lanoline alcohols (Acetulan) | 2% |
| 9. Propoxylated lanoline ether (Solulan PB 10) | 1.5% |
| 10. Butylated hydroxyanisole | 0.02% |
| 11. 2-Phenoxyethanol | 0.5% |
| 12. Propyl para-hydroxybenzoate | 0.4% |
| 13. Butyl para-hydroxybenzoate | 0.2% |
| 14. Carbopol 934 | 0.25% |
| 15. Propylene glycol | 3% |
| 16. Triethanolamine qs   pH ≅ 6.5 | 0.3% |
| 17. Purified water qs | 100% |
| | pH: in the region of 6.5 |

Formula C

| | |
| --- | --- |
| 1. Retinal (trans form) | 0.05% |
| 2. Hybrid safflower oil (Neobee 18) | 10% |
| 3. Heavy liquid petrolatum | 5% |
| 4. Coconut triglycerides (Neobee M5) | 10% |
| 5. Ethoxylated hydrogenated castor oil (Cremophor RH 40) | 1% |
| 6. Glycerol monostearate/PEO (Simulsol 165) | 8.5% |
| 7. Microcrystalline wax (Wax E) | 1.5% |
| 8. Acetylated lanoline alcohols (Acetulan) | 2% |
| 9. Propoxylated lanoline ether (Solulan PB 10) | 1.5% |
| 10. Ronoxan 582 (ascorbyl palmitate) | 0.2% |
| 11. 2 phenoxyethanol | 0.5% |
| 12. Propyl para-hydroxybenzoate | 0.4% |
| 13. Butyl para-hydroxybenzoate | 0.2% |
| 14. Carbopol 934 | 0.25% |
| 15. Propylene glycol | 3% |
| 16. Triethanolamine qs   pH ≅ 6.5 | 0.3% |
| 17. Purified water qs | 100 |
| | pH: in the region of 6.5 |

Formula D

| | |
| --- | --- |
| 1. Retinal (trans form) | 0.05% |
| 2. Hybrid safflower oil (Neobee 18) | 10% |
| 3. Heavy liquid petrolatum | 5% |
| 4. Coconut triglycerides (Neobee M5) | 10% |
| 5. Ethoxylated hydrogenated castor oil (Cremophor RH 40) | 1% |
| 6. Glycerol monostearate/PEO (Simulsol 165) | 8.5% |
| 7. Microcrystalline wax (Wax E) | 1.5% |
| 8. Acetylated lanoline alcohols (Acetulan) | 2% |
| 9. Propoxylated lanoline ether (Solulan PB 10) | 1.5% |
| 10. Propyl gallate | 0.02% |
| 11. 2-Phenoxyethanol | 0.5% |
| 12. propyl para-hydroxybenzoate | 0.4% |
| 13. Butyl para-hydroxybenzoate | 0.2% |
| 14. Carbopol 934 | 0.25% |
| 15. Propylene glycol | 3% |
| 16. Triethanolamine qs   pH ≅ 6.5 | 0.3% |
| 17. Purified water qs | 100% |
| | pH: in the region of 6.5 |

We claim:

1. Dermocosmetological composition comprising retina in 13-cis or 13-trans form or in the form of a mixture of thes isomers, consisting of an oil-in-water emulsion stabilized b a fat-soluble antioxidant consisting of butylated hydrox toluene (BHT), wherein the concentration of retinal is between 0.01 an 1% by weight, wherein the concentration of BHT is between 0.01 an 0.03% by weight, and wherein the BHT/retinal concentration ratio is betwee 0.1 and 0.6.

2. Composition according to claim 1, wherein the retin is present in the oily phase.

3. Composition according to claim 1, wherein the fa soluble antioxidant/retinal concentration ratio is approx mately 0.4.

4. Composition according to claim 1 wherein the pH the composition is between 6 and 7.5.

5. Process for preparing a composition according to clai 1 comprising the following steps:

a) retinal is dissolved in a solvent selected from the grou consisting of an organic oil, a mineral oil, a wax, ester and a silicone or a mixture of two or more therec b) the fat-soluble antioxidant (BHT) is added to the solution, and c) the solution obtained is emulsified in an aqueous or aqueous-alcoholic solution to obtain an oil-in-water emulsion the concentration of retinal being between 0.01 and 1% by weight, the concentration of BHT being between 0.01 and 0.03% by weight, and the BHT/retinal concentration ratio being between 0.1 and 0.6.

6. Composition according to claim 1, comprising retinal at a concentration of approximately 0.05% by weight and BHT at a concentration of approximately 0.02% by weight.

* * * * *

UNITED STATES PATENT AND TRADEMARK OFFICE
CERTIFICATE OF CORRECTION

PATENT NO. : 5,776,986
DATED : July 7, 1998
INVENTOR(S) : Emmanuelle Couval, et al It is certified that error appears in the above-identified patent and that said Letters Patent is hereby corrected as shown below:

On the title page: Item [56]

under FOREIGN PATENT DOCUMENTS, line 1; "European Pat Off." should read -- French Pat. Off. --.
Col. 1, line 3; "PCT/FK95100250" should read -- PCT/FR95/00350 --
Col. 1, line 52; "antioxidant" should read -- antioxidants --.
Col. 3, line 7 of the first table; Delete "0" after the bullet.
Col. 3, line 14 of the first table; Delete the bullet before "ACETATE".
Col. 3, line 5 of TABLE 2; "99.4%" should be -- 98.4% --.
Col. 4, line 6 of TABLE 2; Insert -- 0.1% -- at the beginning of the line.
Col. 4, line 21; Delete "(R).
Col. 4, line 37; "liguid" should read -- liquid --.
Col. 4, line 4 of the second table; Delete the bullet.
Col. 4, line 6 of the second table; Delete the bullet.
Col. 4, line 11 of the second table; Delete the bullet.
Col. 5, lines 7-17 (under the column "T0 T6 months"); all of the

UNITED STATES PATENT AND TRADEMARK OFFICE
CERTIFICATE OF CORRECTION

PATENT NO. : 5,776,986
DATED : July 7, 1998
INVENTOR(S) : Emmanuelle Couval, Nicole Peyrot, Nathalie Firmino, Henri Jammes, and Valerie Clairand It is certified that error appears in the above-identified patent and that said Letters Patent is hereby corrected as shown below:

Contd:

numbers under this column should be moved down one (1) line
Col. 5, line 50; "liqiiid" should read -- liquid --.
Col. 6, line 48; "gs" should read -- qs --.
Col. 7, line 43; "100" should read -- 100% --.
Col. 8, line 20; "100" should read -- 100% --.

Signed and Sealed this

Fifth Day of September, 2000

Attest:

Q. TODD DICKINSON

Attesting Officer    Director of Patents and Trademarks